United States Patent [19]

Schuda et al.

[11] Patent Number: 4,788,322

[45] Date of Patent: Nov. 29, 1988

[54] PROCESS FOR PREPARING ACHPA

[75] Inventors: Paul F. Schuda, New Providence; William J. Greenlee, Teaneck; Prasun K. Chakravarty, Edison; Philip Escola, Spring Lake Heights, all of N.J.

[73] Assignee: Merck & Co., Inc., Rahway, N.J.

[21] Appl. No.: 80,943

[22] Filed: Jul. 31, 1987

[51] Int. Cl.$^4$ .................................. C07C 125/065
[52] U.S. Cl. ............................................ 560/115
[58] Field of Search .................... 560/115; 562/567

[56] References Cited

U.S. PATENT DOCUMENTS

| | | | |
|---|---|---|---|
| 3,969,406 | 7/1976 | Tenud | 562/567 |
| 4,021,480 | 5/1977 | Tenud | 562/567 |
| 4,296,242 | 10/1981 | Tattanahalli | 562/567 |
| 4,487,963 | 12/1984 | Bock | 562/567 |
| 4,681,972 | 7/1987 | Kaltenbronn | 560/115 |

FOREIGN PATENT DOCUMENTS 165226 12/1985 European Pat. Off. .
210896 2/1987 European Pat. Off. .

OTHER PUBLICATIONS

Borch, J. Am. Chem. Soc., 93, pp. 2897–2904 (1971).
Boger, J. Med. Chem., 28, pp. 1779–1790 (1985).

*Primary Examiner*—Michael L. Shippen
*Attorney, Agent, or Firm*—Frank S. Chow; Hesna J. Pfeiffer

[57] ABSTRACT

Process comprising coupling of an acylimidazole-activated derivative of a reduced and protected phenylalanine with the magnesium salt of malonic acid monoethyl ester to produce the beta-ketoester, which is subsequently reduced with NaCNBH$_3$/THF in glacial acetic acid to afford a separable mixture of 3-S and 3-R 3-hydroxy-(4S)-4-(N-α-BOC)amino-5-cyclohexylpentanoic acid, such that large-scale, high yield production of optically-active ACHPA is significantly improved.

2 Claims, No Drawings

PROCESS FOR PREPARING ACHPA

The present invention is concerned with a process for producing (3S, 4S)-(N-αBOC)-4-amino-5-cyclohexyl-3-hydroxypentanoic acid ethyl ester, in large lots with high yields of the (S,S) isomer. By this process, an acylimidazole-activated derivative of a modified amino acid is coupled with the magnesium salt of malonic acid monoethyl ester to afford the β-ketoester. This β-ketoester is then reduced using NaCNBH$_3$/THF in glacial acetic acid to afford a separable 1:1 mixture of 3S and 3R 3-hydroxy-(4S)-4-(N-α-BOC)amino-5-cyclohexyl-pentanoic acid which can be purified to enantiomerically-pure (3S, 4S) material by crystallization and, e.g., silica gel chromatography.

The (3S,4S)-(Nα-BOC)-4-amino-5-cyclohexyl-3-hydroxypentanoic acid ethyl ester (the ethyl ester of BOC-protected ACHPA) has been successfully substituted for the 10,11 peptide bond (by substrate analogy numbering) in potent peptide renin-inhibitors.

BACKGROUND OF THE INVENTION

Renin is an endopeptidase (molecular weight about 40,000) produced and secreted by the juxtaglomerular cells of the kidney, which cleaves its plasma substrate, angiotensinogen, specifically at the 10, 11 peptide bond, i.e., between Leu 10 and Leu 11 in the equine substrate, as described by Skeggs et al., *J. Exper. Med.* 1957. 106, 439, or between the Leu 10 and Val 11 in the human renin substrate, as elucidated by Tewksbury et al., *Circulation* 59, 60, Supp. II: 132, Oct. 1979. Renin cleaves angiotensinogen to split off the decapeptide, angiotensin I, which is converted by angiotensin-converting enzyme to the potent pressor substance angiotensin II. Thus, the renin-angiotensin system plays an important role in normal cardiovascular homeostasis and in some forms of hypertension.

Inhibitors of angiotensin I converting enzyme have proven useful in the modulation of the renin-angiotensin system and consequently, specific inhibitors of the limiting enzymatic step that ultimately regulates angiotensin II production, the action of renin on its substrate, have also been sought as effective investigative tools and as therapeutic agents in the treatment of hypertension and congestive heart failure.

Renin antibody, pepstatin, phospholipids, and substrate analogs, including tetrapeptides and octa- to tridecapeptides, with inhibition constants (K$_i$) in the $10^{-3}$ to $10^{-6}$M region, have been studied.

Umezawa et al., in *J. Antibiot.* (*Tokyo*) 23: 259–262, 1970, reported the isolation of a peptide, pepstatin, from actinomyces that was an inhibitor of aspartyl proteases such as pepsin, cathepsin D, and renin. Gross et al., *Science* 175:656, 1972, reported that pepstatin reduces blood pressure in vivo after the injection of hog renin into nephrectomized rats, but pepstatin has not found very wide application as an experimental agent because of its limited solubility and its inhibition of a variety of other acid proteases in addition to renin.

Many efforts have been made to prepare a specific renin inhibitor based on pig renin substrate analogy, which as been shown to correlate well with and predict human renin inhibitor activity. The octapeptide amino acid sequence extending from histidine-6 through tyrosine-13

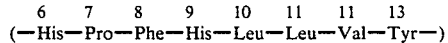

has been shown to have kinetic parameters essentially the same as those of the full tetradecapeptide renin substrate.

Kokubu et al., *Biochem. Pharmacol.,* 22, 3217–3223, 1973, synthesized a number of analogs of the tetrapeptide found between residues 10 to 13, but while inhibition could be shown; inhibitory constants were only of the order of $10^{-3}$M. Analogs of a larger segment of renin substrate were synthesized, Burton et al., *Biochemistry* 14: 3892–3898, 1975, and Poulsen et al., *Biochemistry* 12: 3877–3882, 1973, but a lack of solubility and weak binding (large inhibitory constant) have proven to be major obstacles to obtaining effective renin inhibitors.

Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success.

Modifications designed to increase binding to renin have also been made, but here too, with mixed results.

Powers et al., in *Acid Proteases, Structure, Function and Biology,* Plenum Press, 1977, 141–157, have suggested that in pepstatin, statine occupies the space of the two amino acids on either side of the cleavage site of a pepsin substrate, and Tang et al., in *Trends in Biochem. Sci.,* 1:205–208 (1976) and *J. Biol. Chem.,* 251:7088–94, 1976, have proposed that the statine residue of pepstatin resembles the transition state for pepsin hydrolysis of peptide bonds. Inhibitors of renin which contain the amino acid statine have been disclosed in the following: Veber et al, U.S. Pat. No. 4,384,994; European Published Application No. 77 029; Evans et al, U.S. Pat. No. 4,397,786; Veber et al, EP-A No. 77 028; Boger et al, *Nature,* 1983, 303, 81–84; U.S. Pat. No. 4,470,971; EP-A No. 114 993 and No. 157 409; U.S. Pat. No. 4,485,099; Matsueda et al, EP-A No. 128 762, 152 255; Morisawa et al., EP-A No. 186 977; Riniker et al, EP-A No. 11 266; Bindra et al, EP-A No. 55 809; Stein et al, *Fed. Proc.* 1986, 45, 869; and German Patent Application DE No. 3438-545-A.

Renin inhibitors containing other peptide bond isosteres, including a reduced carbonyl peptide bond isostere are disclosed by M. Szelke et al, in work described in published European Patent Application Nos. 45 665, 104 041, U.S. Pat. No. 4,424,207, and in PCT Int. Appl. WO No. 84 03,044; *Nature,* 299, 555 (1982); *Hypertension,* 4, Supp. 2, 59, 1981; British Pat. No. 587,809; and in *Peptides, Structure and Function: Proceedings of the Eighth American Peptide Symposium,* ed. V. J. Hruby and D. H. Rich, p. 579, Pierce Chemical Co., Rockford, Ill., 1983, where substitution at the Leu-Leu site of renin cleavage by isosteric substitution, resulted in compounds with excellent potency. Other peptide bond isosteres have been disclosed in Buhlmayer et al in EP-A No. 144 290 and No. 184 550; Hester et al. EP-A No. 173 481; Raddatz, EP-A No. 161 588; Dann et al, *Biochem. Biophys. Res. Commun.* 1986, 134, 71–77; Fuhrer et al., EP-A No. 143 746; Kamijo et al, EP-A No. 181 110; Thaisrivongs et al. *J. Med. Chem.,* 1985, 28, 1553–1555; Ryono et al., EP-A No. 181 071; and Evans et al., U.S. Pat. No. 4,609,641.

Of these non-statine peptide bond isosteres, (3S, 4S)-4-amino-5-cyclohexyl-3-hydroxypentanoic acid (ACHPA, an analog of statine in which the isobutyl group has been replaced by a cyclohexylmethyl group), when substituted for statine in a renin inhibitor, has often resulted in inhibitors that are 50-fold more potent than the corresponding statine-containing analogs. Previous methods for synthesizing the necessary protected derivative of enantiomerically-pure ACHPA for producing these useful renin inhibitors, however, have been limiting. See, e.g., Boger et al., *J. Med. Chem.* 1985, 28, 1779–1790, wherein low yields, difficulties in scale-up and the ease of racemization of the reductively-derived alpha-amino aldehydes produced significantly impeded development of potent, orally-active inhibitors of renin.

Descamps et al., in EPO published application No. 165 226 (1985), described a synthesis of (3S, 4S)-(Nα-BOC-4-amino-5-cyclohexyl-3-hydroxypentanoic acid methyl ester, in which the magnesium salt of malonic acid monomethyl ester is used to prepare a keto ester intermediate, which is subsequently reduced to yield the product as a mixture of (3S, 4S) and (3R, 4S) diastereomers. However, the yield of the desired (3S, 4S) diastereomer in the reduction step is low (15%) and the Raney nickel used for the reduction can cause racemization during the reduction step. Further, the separation step comprises silica gel chromatography of the crude reduction product, containing both (3S, 4S) and (3S, 4S) diastereomers, which represents a limitation to scale-up to preparing large lots of material. Then, in a 1987 reference, Jouin et al., EPO published application No. 210 896, ACHPA was prepared starting from Meldrum's Acid, a less-readily available starting material.

It was therefore an object of this invention to develop a method of synthesizing ACHPA which experienced minimal racemization and consequently little loss of optical activity. It was also an object to develop a process which could be scaled-up to allow production of optically-active ACHPA in large lots.

DESCRIPTION OF THE INVENTION

The present invention is directed to a process for preparing optically-pure (3S,4S)-(Nα-BOC)-4-amino-5-cyclohexyl-3-hydroxypentanoic acid ethyl ester (Nα-BOC-(S,S)-ACHPA-OEt) comprising coupling an acylimidazole-activated derivative of a modified natural amino acid with the magnesium salt of malonic acid monoethylester to afford the β-ketoester which is then reduced using NaCNBH3/THF in glacial acetic acid to afford a separable 1:1 mixture of 3-S and 3-R derivatives, which can be purified by, e.g., crystallization and silica gel chromatography, to the enantiomerically-pure (S,S) material.

Specifically, the process may be represented by the schematic:

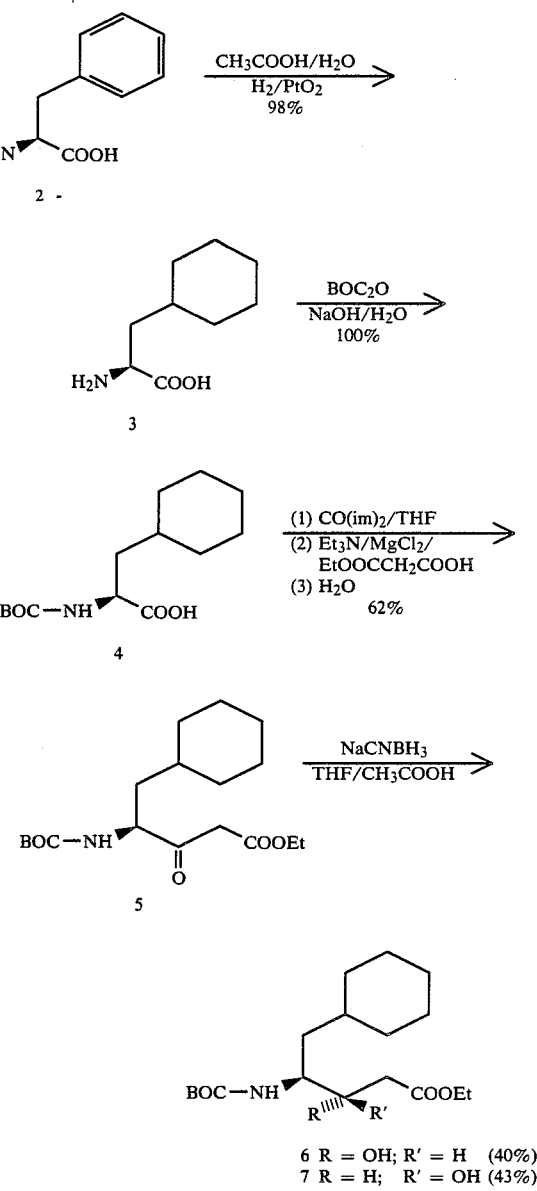

According to this process, L-phenylalanine (2) is reduced to the hexahydro acid (3) with 98% PtO2, and protected as the N-α-t-BOC derivative using Schotten-Baumen conditions to produce the compound of structure 4 (100%). Then, in one pot, a two-carbon homologation sequence is accomplished by sequential formation of the imidazolide derivative, and addition of a mixture of malonic acid monoethyl ester/MgCl2 (anh-)/Et3N, and standard workup to give the β-ketoester (5) as a thick oil (62% yield). Direct hydride reduction of the β-ketoester using NaCNBH3/THF in the presence of glacial acetic acid affords a 1:1 mixture of N-α-BOC-(S,S)-ACHPA-OEt (6) and the undesired 3R, 4S isomer (7) with minimal racemization at C-4. The undesired isomer 7, which crystallizes more easily, is removed in that way, and the thereby-enriched desired isomer 6 is purified by silica gel chromatography to give the optically-pure material (40%), with an enantiomeric purity determined to be 92.4–92.7% ee by HPLC analysis of the 2,3,4,6-tetrahydro-O-acetyl-β-D-glucopyranosyl isothiocyanate (GITC) derivative.

By this process, with the substitution of the cyanoborohydride NaCNBH₃/THF(anh/HOAc) in place of e.g., NaBH₄, LiAl(OtBu)₃H, Zn (BH₄)₂ or the like, for the standard hydride reduction of the β-ketoester (5), a 1:1 mixture of the isomers 6 and 7 is achieved, rather than predominantly the undesired 3R, 4S isomer 7. With catalytic hydrogenation (RaNi/H/EtOH/65° C.), this predominance of undesired isomer 7 can be converted to a 1:1 mixture of 6 and 7, but at the expense of significant (ca. 15%) racemization of the C-4 center. Thus, the easy racemization of the 2S-(N-α-BOC)-2-amino-3-cyclohexyl-propionaldehyde upon addition of organometallic reagents, and the consequent loss of optical activity, is avoided. Easy scale-ups to much larger lots with much higher yields of a key central unit for peptide renin inhibitors is now realizable.

Having economically-viable quantities of an enantiomerically-pure protected derivative of ACHPA available then results in more practical production of orally-active renin inhibitors for therapeutic treatment of renin-associated hypertension, hyperaldosteronism and/or congestive heart failure or for vivo or in vitro diagnostic methods for establishing the significance of renin as a causative or contributory factor of these conditions in a particular patient.

The following example is intended to be representative and not limiting.

EXAMPLE 1

Preparation of (3S)-3-hydroxy-(4S)-4-(N-α-BOC)amino-5-cyclohexyl-pentanoic acid

Step A: 2-Amino-3-hexahydrophenylpropionic acid (3)

A solution of 50.00 g (0.303 moles) of L-phenylalanine (2) in 200 mL of glacial acetic acid and 140 mL of water was treated with 2.50 g of platinum oxide and the mixture hydrogenated at 45 psig of hydrogen at 50° C. for 18 hours on a Parr Shaker apparatus. The reaction mixture was cooled to room temperature, the semi-solid mass dissolved by adding additional acetic acid and methanol (ca. 100 mL each), and the solution was filtered through a small pad of celite, with the pad being washed with additional methanol.

The combined filtrates were evaporated completely in vacuo and the remaining solid triturated with anhydrous ether (2×500 mL) and filtered. The white solid was air dried by suction filtration to afford 50.80 g (98%) of 2-amino-3-hexahydrophenylpropionic acid (3) as a white powder, m.p. (Haake-Buchler apparatus, uncorrected) 295°–297° C. (begins to sublime at 290° C. NMR (proton nuclear magnetic resonance spectra on a Varian XL-300 spectrometer, with all shifts reported as ppm downfield from tetramethylsilane) (D₂O; 300 MHz) δ 0.80–1.00 (m, 2H), 1.05–1.46 (m, 4H), 1.50–1.80 (m, 7H), 3.72 (dd, 1H) ppm; IR (infrared spectra on a Perkin-Elmer 283 spectrometer, calabrated against the 1601 cm⁻¹ band of polystyrene) (CHCl₃) 3500–2400 (v br), 1580 cm.

Step B: N-α-BOC-Amino-3-hexahydrophenylpropionic acid (4)

2-Amino-3-hexahydrophenylpropionic acid (3) (45.00 g, 0.263 moles) was dissolved in a mixture of 580 mL of 0.5N sodium hydroxide and 450 mL of dioxane. The resulting solution was cooled to 0° C., treated dropwise with 63.11 g (66.50 mL, 0.290 moles) of di-tert-butyl dicarbonate over a period of about 30 minutes, and the reaction mixture was allowed to warm to room temperature of its own accord (ca. 3 hours), then stirred vigorously for an additional 17 hours. Most of the volatiles were evaporated in vacuo and the remaining solution cooled to 0° C. and acidified to pH of 1-to-2 with 1N KHSO₄.

The resulting mixture was extracted with 3×200 mL of methylene chloride, the combined organic solutions dried over anhydrous sodium sulfate, and the volatiles evaporated in vacuo. This afforded 71.30 g of N-α-BOC-amino-3-hexahydrophenylpropionic (4) (100%) as a very viscous, colorless oil that was very pure by spectroscopic analysis. NMR (CDCl₃; 300 MHZ) δ 0.75–1.30 (m, 6H, 1.42 (s, 9H), 1.43–1.84 (m, 7H), 4.33 (m, 1H), 4.82 (d, J=7.5 Hz, 1H) ppm; IR (CHCl₃) 3500–2550 (v br), 3450, 2950, 1710, 1160 cm⁻¹.

Step C: 3-Oxo-(4S)-4-(N-α-BOC)amino-5-cyclohexyl-pentanoic acid ethyl ester (5)

Imidazolide solution: A solution of the carboxylic acid (4) of Step B (1060 g, 3.90 moles) in 7L of tetrahydrofurn was stirred at room temperature while 705 g (4.35 moles) of 1,1-carbonyldiimidazole was added in portions of ca. 100 g. each. Strong gas evolution ocurred, but there was no increase in temperature of the reaction.

The solution was then allowed to stir at room temperature for 20 hours, during which period the solution became slightly yellow.

Magnesium malonate solution: A solution of 567 g (4.30 moles) of malonic acid monoethyl ester in 5L of tetrahydrofuran was cooled to 0° C. in a methanol-ice bath, and Magnesium chloride (225 g., 2.40 moles) was added all in one portion, followed by the dropwise addition of 480 g (660 mL, 4.73 moles) of triethylamine over a period of ca. 20 minutes in order that the temperature of the reaction not exceed 10° C. The reaction mixture became a white slurry and was stirred at 0° C. for one hour.

The slurry from the magnesium malonate solution was then added all at once to the imidazolide solution at room temperature. The residue from the malonate solution was rinsed in with a small amount of tetrahydrofurn and mixture was concentrated in vacuo (ca. 90% of the THF was removed) and the residue partitioned between 5L of ether and 5L of water, which layers were separated. The aqueous layer was extracted with 3×3L portions of ether and the combined organic layers were washed with 3×1L of water, and 1×1L of saturated NaCl, then dried over sodium sulfate and magnesium sulfate, and concentrated in vacuo to afford 1261 g of a viscous material as the crude product.

The crude material was dissolved in 3L of methylene chloride and filtered through 3 kg of silica gel (70–230 mesh) in a large sintered glass funnel, with additional methylene chloride (25L) being used to elute the desired ketone from the silica gel. Evaporation of the solvent afforded 822 g (62%) of desired ketone 5 as a viscous oil. [α]$_D$ = −38.4° (c=1; MeOH); NMR (CDCl₃; 300 MHz) δ 0.80–1.42 (m, containing 3H t at δ 1.28, 13H), 1.45 (s, 9H), 1.53–1.92 (m, 2H), 3.51 (d, J=14.4 Hz, 1H), 3.58 (d, J=14.4 Hz, 1H), 4.19 (q, 2H), 4.39 (m, 1H), 4.90 (d, J=7.8 Hz, 1H) ppm; IR (CHCl₃) 2950, 1710, 1485, 1370, 1145 cm⁻¹.

Step D:
(3S)-3-Hydroxy-(4S)-4-(N-α-BOC)amino-5-cyclohexylpentanoic acid (6) and
(3R)-3-hydroxy-(4S)-4-(N-α-BOC)amino-5-cyclohexylpentanoic acid (7)

A solution of 612 g (1.80 moles) of ketoester (5) in 6L of tetrahydrofuran was cooled in an ice bath and treated with 126 g (2 moles) of sodium cyanoborohydride. The resulting solution was stirred, treated with 355 g (340 mL, 5.90 moles) of glacial acetic acid, added dropwise over a period of 20 minutes, and the ice bath was removed. The reaction mixture was then stirred at room temperature for 16 hours.

The resulting mixture was concentrated under reduced pressure to about 20% of the original volume and added to 2L of water. Ther water was extracted with 4×1L of ether and the combined ether layers were washed with 1L of water, then with 500 mL portions of saturated sodium bicarbonate until the aqueous was neutral pH. The organic solution was wahed with 1L of water and 1L saturated NaCl, then dried over sodium sulfate and magnesium sulfate, and concentrate in vacuo to afford 717 g of a thick golden oil.

Hexane (700 mL) was added to the oil and the mixture heated until a clear yellow solution was obtained. The solution was allowed to cool, and the flask was scratched to induce crystallization, and cooled in a refrigerator for ca. 20 hours. The solid was filtered off, washed with a small amount of cold hexanes and dried in vacuo, then recrystallized from 400 mL of hexanes to afford 176 g of pure 3R, 4S material (7).

The combined mother liquors from above were concentrated under reduced pressure and the enriched mixture was completely separated by preparative HPLC using a Waters Prep 500 utilizing 2 silica gel packs and 9% acetone in hexanes as the eluant (flow rate=250 mL/minute). The appropriate fractions were combined and the solvents evaporated under reduced pressure, to afford 245 g (40%) of desired 3S,4S isomer (6) and 266 g (43%) of 3R,4S isomer (7).

(3S), 4S) 6: m.p 67°–69° C.; $R_f$=0.35 (20% acetone in hexanes); $[\alpha_D = -32°$ (c=1.4; MeOH) (lit. ref. 2; $-34°$); NMR (CDCl$_3$; 300 MHz) δ 0.80–1.92 (m containing 3 H t at δ 1.28 and 9 Hs at δ 1.44, 13H), 2.40–2.62 (m, 2H), 3.26 (br s, 1H), 3.60–3.70 (m, 1H), 4.01 (d, J=9.0 Hz, 1H), 4.18 (q, 2H), 4.69 (d, J=9.6 Hz, 1H) ppm; IR (CHCl$_3$) 3460 (br), 2940, 1705, 1490, 1165 cm$^{-1}$.

(3R),(4S): m.p. 81°–83° C.; Rf=0.25 (20% acetone in hexanes); $[\alpha]_D = -16.7°$ (c=1.6; MeOH); NMR (CDCl$_3$; 300 MHz) δ 0.70–1.92 (m, containing 3H t at δ 1.28 and 9H s at δ 1.45, 13H), 2.41–2.52 (m, 2H), 3.40 (br s, 1H), 3.62–3.78 (m, 1H), 4.00 (m, 1H), 4.17 (q, 2H), 4.54 (d, J=10.2 Hz, 1H) ppm; IR (CHCl$_3$) 3450 (br), 2930, 1700, 1485, 1445, 1370, 1165, 1030 cm$^{-1}$.

What is claimed is:

1. A process for preparing (3S, 4S)-(N-α-BOC)-4-amino-5-cyclohexyl-3-hydroxypentanoic acid ethyl ester comprising treatment of N-α-BOC-amino-3-hexahydrophenylpropionic acid with 1,1-carbonydiimidazole to form an acylimidazole-activated derivative of N-α-BOC-amino-3-hexahydrophenylpropionic acid, then (a) coupling said acylimidazole-activated derivative with the magnesium salt of malonic acid monoethylester to afford the β-ketoester;
    (b) reducing said β-ketoester using sodium cyanoborohydride in tetrahydrofuran and glacial acetic acid to produce a mixture of (3S,4S)-(Nα-BOC)-4-amino-5cyclohexyl-3-hydroxypentanoic acid ethyl ester and (3S,4S)-(Nα-BOC)-4-amino-5-cyclohexyl-3-hydroxypentanoic acid ethyl ester; and
    (c) crystallizing off the (3R,4S) compound and purifying the remaining product to afford optically-pure (3S,4S)-(Nα-BOC)-4-amino-5-cyclohexyl-3-hydroxypentanoic acid.

2. A process according to claim 1, wherein the product remaining after the (3R,4S) compound is crystallized off is purified with silica gel chromotagraphy.

* * * * *